United States Patent [19]

Ueno et al.

[11] 4,218,918
[45] Aug. 26, 1980

[54] DEVICE FOR SAMPLING GASES IN BLAST FURNACE

[75] Inventors: Masayuki Ueno, Yokohama; Makoto Sagae, Tokyo; Fumiaki Sano, Yokohama, all of Japan

[73] Assignee: Ishikawajima-Harima Jukogyo Kabushiki Kaisha, Tokyo, Japan

[21] Appl. No.: 955,535

[22] Filed: Oct. 30, 1978

[30] Foreign Application Priority Data

Nov. 18, 1977 [JP] Japan ................. 52-138724

[51] Int. Cl.³ ............................................. G01N 1/22
[52] U.S. Cl. ............................................. 73/421.5 R
[58] Field of Search ................. 73/421.5 R, 421.5 A

[56] References Cited

U.S. PATENT DOCUMENTS 3,152,479  10/1964  Small .............................. 73/421.5 A
4,054,060  10/1977  Ueno et al. ..................... 73/421.5 A Primary Examiner—S. Clement Swisher
Attorney, Agent, or Firm—Scrivener, Parker, Scrivener and Clarke

[57] ABSTRACT

A device is disclosed for inserting a lance into a vertical furnace, especially a blast furnace, so as to sample gases and measure the temperatures or pressures thereof, thereby obtaining the accurate information of operating conditions in the furnace.

5 Claims, 7 Drawing Figures

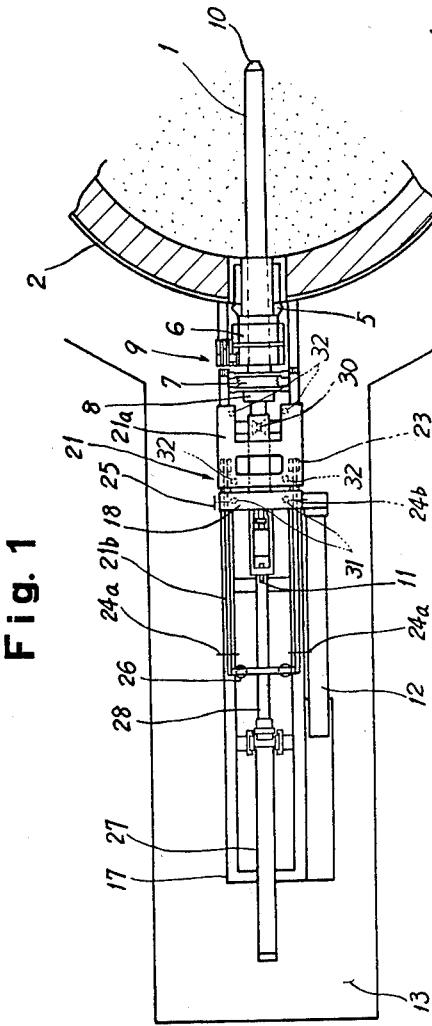
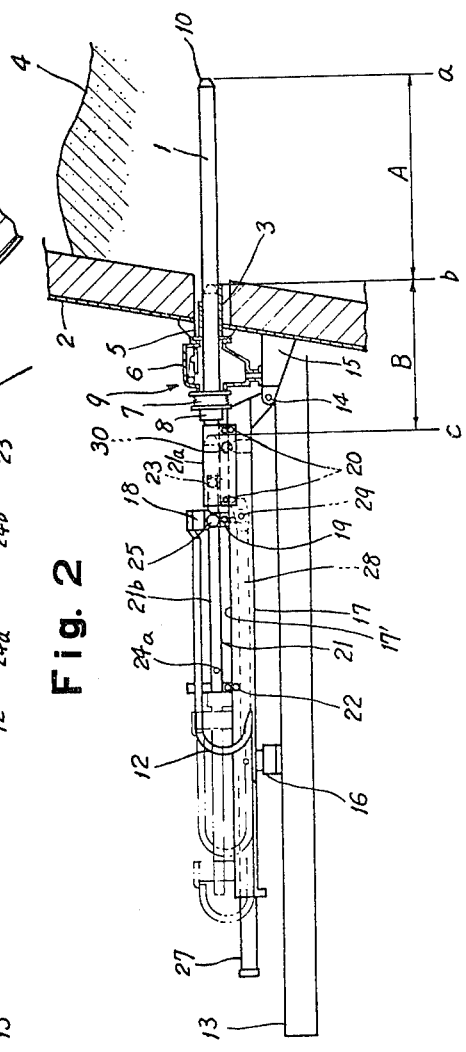
Fig. 1
Fig. 2

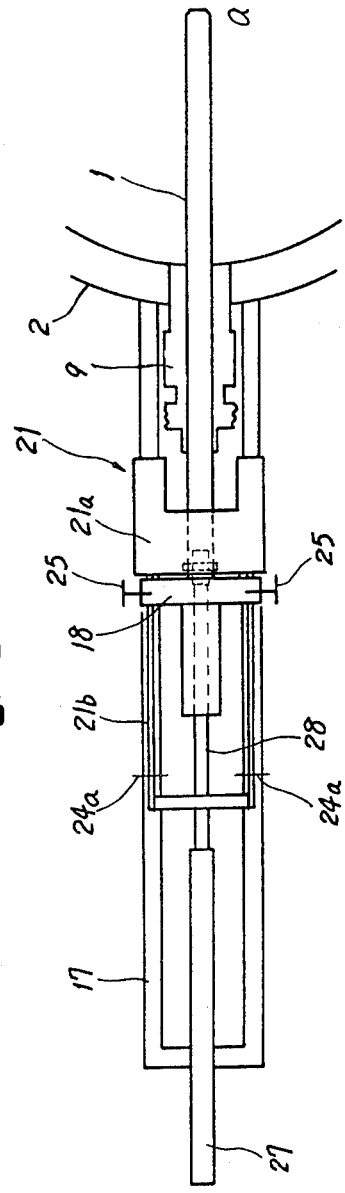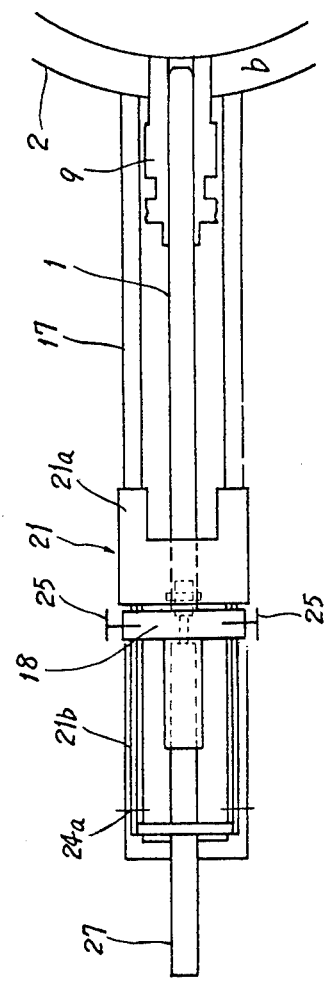

DEVICE FOR SAMPLING GASES IN BLAST FURNACE

DETAILED DESCRIPTION OF THE INVENTION

The present invention relates to a device for sampling gases in a blast furnace or the like.

With increases in the working volume and the pressure of blast air of the recently constructed blast furnaces, it is increasingly essential to ensure stable and highly efficient furnace operations and to attain raw material savings. To this end, the gas sampling devices are now an indispensable instrument.

The prior art gas sampling devices are in general equipped with a lance driving cylinder whose stroke is equal to the distance between the sampling or measuring position of the probe end of a lance and the emergency or maintenance position at which the probe end of the lance is completely withdrawn from the furnace. As a result, the overall length of the prior art gas sampling devices becomes long, resulting in the reduction in strength resisting against buckling and in increase in installation space. Furthermore, the prior art gas sampling devices of the type using two driving cylinders need a synchronization device which is expensive, thus resulting in the increase in weight and cost.

In view of the above, one of the objects of the present invention is to provide a device for sampling gases in a blast furnace or the like which is equipped with a cylinder of short length so that the overall length of the gas sampling device may be made short and compact in size.

Another object of the present invention is to provide a device for sampling gases in a blast furnace or the like which is very economical.

A further object of the present invention is to provide a device for sampling gases in a blast furnace or the like whose installation space may be minimized.

Another object of the present invention is to provide a device for sampling gases in a blast furnace or the like which is less likely to buckle.

A still further object of the present invention is to provide a device for sampling gases in a blast furnace or the like which is highly reliable and dependable in operation.

A yet another object of the present invention is to provide a device for sampling gases in a blast furnace or the like which is very simple in construction and which may be feasible by small modifications of the existing gas sampling devices.

The present invention will become apparent from the following description of preferred embodiments thereof taken in conjunction with the accompanying drawings, in which:

FIG. 1 is a top view of a first embodiment of a device for sampling gases in a blast furnace or the like in accordance with the present invention;

FIG. 2 is a side view thereof;

FIG. 3 shows a lance at the sampling or measuring position;

FIG. 4 shows the lance at the normal retracted position;

Same reference numerals are used to designate similar parts throughout the figures.

Figure 5:
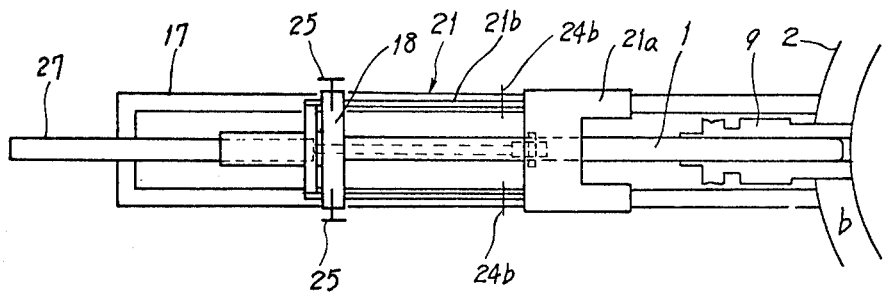
FIG. 5 shows the step for further retracting the lance to the emergency or maintenance position.

Referring to FIGS. 1 and 2, a lance 1 may be slidably inserted radially inwardly into the charge 4 in the furnace through a bush 3 attached to a lance insertion hole formed through the furnace wall of the shaft of the furnace. In order to air-tightly seal the lance 1, a sealing mechanism 9 is provided which comprises a swing check valve 6 bolted to a nozzle portion 5 extended outwardly from the shell 2, a bellows 7 and a sealing device 8.

The probe end 10 of the lance is provided with the measuring junction of a thermocouple and is formed with a gas sampling hole. A cylinder 11 is connected to the rear end of the lance 1 so as to open and close the probe end 10. The lance 1 is so constructed as to be cooled with water. Extended out of the rear end of the lance 1 are the lead wires of the thermocouple, the lead wires of limit switches which control the stroke of the cylinder 11, hydraulic lines, a rubber hose for sampling the gases in the furnace and purging the nitrogen gas, and cooling water hoses. These lead wires, hydraulic lines and hoses are flexibly supported by a cable bearer 12 so that they may follow the stroke of the lance 1 and are connected to the respective wires, pipes and the like exterior to the gas sampling device.

The lance 1 is displaced between the measuring position a and the retracted position b spaced apart from the former by A as best shown in FIG. 2. However, in case of the emergency and inspection and maintenance of the lance which is made a few times every year, the lance 1 must be further retracted away from the retracted position b to the emergency or maintenance position c spaced apart from the former by B.

The most important feature of the present invention is the provision of means for facilitating the retraction of the lance to the emergency or maintenance position c as will be described in detail below. A deck 13 is rigidly attached to the shell 2 and a guide frame 17 is mounted on the deck 13 and supported by a support 16. The front end of the guide frame 17 is connected with pins 14 to brackets 15 extended from the shell 2. A lance supporting bracket 18 which supports the rear end of the lance 1 has pairs of upper and lower wheels 19 which rotate along the upper and lower surfaces, respectively, of guide rails 17' mounted on the guide frame 17. The lance supporting bracket 18 is further provided with side rollers 31 which roll along the interior surfaces of the side walls of the guide rails 17'.

In order to advance or retract the lance 1, a coupling and driving device 21 is provided which comprises in general a front carriage 21a and a coupling frame 21b which is substantially U-shaped when viewed from above as shown in FIG. 1 and is normally linked to the front carriage 21a with pins 23. The front carriage 21a has front and rear pairs of upper and lower wheels 20 which rotate along the upper and lower surfaces, respectively, of the guide rails 17'. The front carriage 21a is further provided with front and rear pairs of side rollers 32 which roll along the interior surfaces of the side walls of the guide rails 17'. The coupling frame 21b which is so constructed and arranged as not to interfere with the free travel of the lance supporting bracket 18 along the guide rails 17' has pairs of upper and lower wheels 22 which are carried at the rear end of the coupling frame 21b and which rotate along the upper and lower surfaces, respectively, of the guide rails 17'.

The coupling frame 21b has two pairs of coupling holes 24a and 24b which are spaced apart from each other in the longitudinal direction. Coupling pins of coupling means 25 provided against both side of the lance supporting bracket 18 are selectively inserted into the coupling holes 24a or 24b as will be described in more detail hereinafter so that the coupling frame 21b is coupled to the lance supporting bracket 18. The coupling frame 21b is further provided with side rollers 26 adjacent the rear end thereof which roll along the interior surfaces of the side walls of the guide rails 17'.

A lance driving cylinder 27 is mounted on the guide frame 17 in parallel with the extended axis of the lance 1 and immediately below it. The free end of a rod 28 of the lance driving cylinder 27 is connected with a pin 29 to the lower rear end of the carriage 21a. The stroke of the lance driving cylinder 27 is equal to the normal lance stroke A when it is longer than the emergency or maintenance stroke B or vice versa. (With the recently constructed large blast furnaces, the stroke A is longer than the stroke B so that the stroke of the lance driving cylinder 27 is always equal to the stroke A.) The distance between the front and rear coupling holes 24a and 24b of the coupling frame 21b is equal to the stroke B.

A lance supporting roller 30 is mounted on the guide frame 17 adjacent to the sealing mechanism 9 so as to support the lance 1 when the latter is completely withdrawn out of the bush 3.

Next referring further to FIGS. 3-6, the mode of operation of the blast furnace gas sampling device with the above construction will be described. When the coupling means or pins 25 of the lance supporting bracket 18 are fitted into the front coupling holes 24b of the coupling frame 21b as shown in FIG. 3 or 4 and when the lance driving cylinder 27 is extended, the lance 1 is advanced in unison with the lance supporting bracket 18 and the coupling and driving device 21 so that the probe end 10 is inserted to the measuring position a in the furnace as shown in FIG. 3. When the lance driving cylinder 27 is retracted, the lance 1 is retracted in unison with the lance supporting bracket 18 and the coupling and driving device 21 so that the probe end 10 is retracted to the inoperative position b as shown in FIG. 4.

Figure 6:
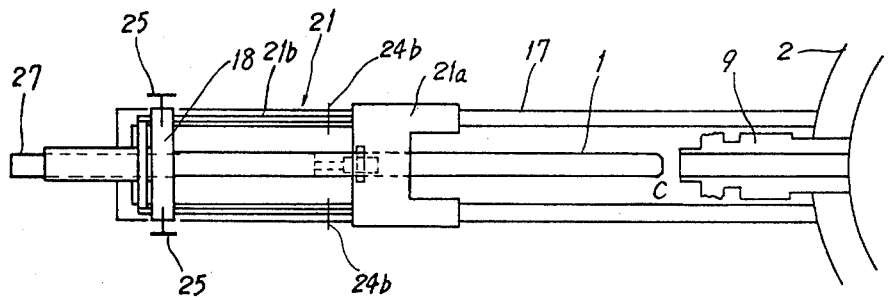
FIG. 6 shows the lance at the emergency or maintenance position.

In the case of the periodic inspection and maintenance or of the emergency, the lance 1 must be completely withdrawn out of the furnace. In this case, the coupling means or pins 25 are pulled out of the front coupling holes 24b of the coupling frame 21b when the lance 1 is retracted to the normal retracted position b shown in FIG. 4. Thereafter the lance driving cylinder 27 is extended so as to advance the coupling and driving device 21. In this case, since the lance supporting bracket 18 is disconnected from the coupling frame 21b, it remains stationary so that the lance 1 may remain in the retracted position b. When the coupling means or pins 25 of the lance supporting frame 18 are in line with the rear coupling holes 24a of the coupling frame 21b, the driving cylinder 27 is de-energized. Then the coupling means or pins 25 of the lance supporting bracket 18 are inserted into the rear coupling holes 24a so that the lance supporting bracket 18 may be coupled to the coupling frame 21b again as shown in FIG. 5. Thereafter the driving cylinder 27 is retracted so that the lance supporting bracket 18 with the lance 1 connected thereto may be retracted in unison with the coupling and driving device 21 to the emergency or maintenance position c as shown in FIG. 6. Returning the lance 1 to the position b from the position c is in reverse sequence. That is, the coupling means or pins 25 of the lance supporting bracket 18 are pulled out of the rear coupling holes 24a and inserted into the front coupling holes as shown in FIG. 3 or 4.

It is to be understood that the present invention is not limited to the embodiment described above. For instance, the driving cylinder, the coupling frame and the lance may be disposed in any suitable manner as long as their axes are parallel with each other. Therefore the lance driving cylinder may be disposed above the coupling frame and the lance. The guide frame and lance may be also disposed in any suitable manner as long as they are in parallel with each other.

Figure 7:
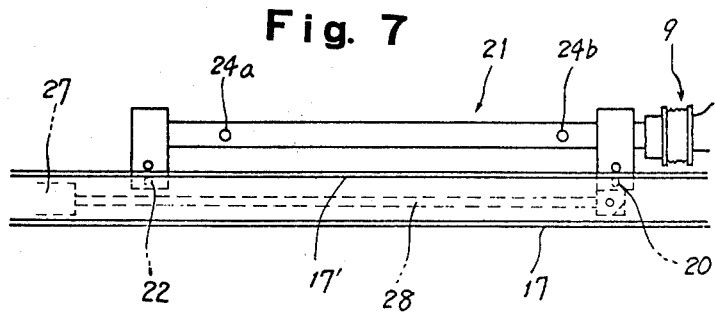
FIG. 7 is a longitudinal side view of a second embodiment of the present invention.

In the first embodiment described above, the coupling and driving device 21 is divided into the front carriage 21a and the coupling frame 21b, but in the second embodiment shown in FIG. 7, they are made into a unitary construction. The coupling and driving device 21 is provided with the coupling holes 24a and 24b. The second embodiment is advantageous over the first embodiment in that the construction may be considerably simplified.

In the second embodiment, the driving cylinder and the coupling and driving device may be disposed in any suitable manner as long as their axes are in parallel with each other. The driving cylinder may be therefore disposed above the lance. In like manner, the guide frame and the lance may be disposed in any suitable manner as long as their axes are in parallel with each other. Furthermore many modifications may be effected without departing from the true spirit of the present invention.

One of the most important features of the coupling and driving device 21 in accordance with the present invention is to simplify the coupling and de-coupling between the lance 1, more particularly the lance supporting bracket 18 and the coupling and driving device 21 without displacing the pivotal point of the driving cylinder 27 because the coupling and driving device 21 is provided with the front and rear coupling holes 24a and 24b spaced apart from each other by the distance equal to the distance or stroke B. Another feature is that since the coupling and driving device 21 has a relatively long length, the moment which is produced by the parallel arrangement of the driving cylinder 27 and the lance 1 and which tends to cause the coupling and driving device 21 to turn about an axis perpendicular to the longitudinal axis thereof may be decreased resulting in the reduction in the reaction forces vertically acting on the front and rear pairs of wheels of the coupling and driving device 21, whereby the overall length of the gas sampling device may be shortened.

According to the present invention, the overall length of the gas sampling device wherein the cylinder is used for advancing or retracting the lance may be so shortened that it may be almost equal to the retraction stroke of the lance. As a result, the installation space may be remarkably reduced. Furthermore only one cylinder suffices to advance and retract the lance so that the gas sampling device may be made light in weight and may attain considerably cost saving. Moreover, since the normal coupling distance or length between the lance and the coupling and driving device can be made shorter so that the strength of the coupling and driving device against buckling may be increased. In addition, the synchronization mechanism may be eliminated which is used in the gas sampling device of the type using two driving cylinders.

What is claimed is:
1. Apparatus for sampling gases in a blast furnace one wall of which contains an access opening, comprising
   (a) a generally horizontal fixed guide frame (17) adapted for mounting on the blast furnace wall adjacent the opening;
   (b) probe means (10) for determining a condition of the blast furnace gases;
   (c) bracket means (18) connecting said probe means with said guide frame for axial displacement relative to the opening between a fully-inserted measuring position (a), a partially withdrawn retracted position (b), and a fully withdrawn maintenance position (c); and (d) drive means for operating said bracket means, said drive means including
       (1) a single piston-cylinder motor (27) connected with said guide frame in parallel spaced relation relative to the axis of said probe means; and
       (2) coupling means for connecting the rod (28) of said motor with said bracket means, said coupling means including
           (a) carriage means (21a) slidably connected with said guide frame for displacement in a direction parallel with the axis of said probe;
           (b) a coupling frame (21b) slidably connected with said guide frame and connected with said carriage means for displacement in a direction parallel with the axis of said probe, said coupling frame and said carriage means being arranged on opposite sides of said bracket means; and
           (c) means (24a, 24b, 25) selectively connecting said bracket means with longitudinally spaced portions of said coupling frame, respectively, whereby owing to the laterally offset relation of said drive means relative to said probe means, buckling of said probe means and the drive means is avoided.

2. Apparatus as defined in claim 1, wherein said bracket, coupling frame and carriage means each include wheel (19, 20, 22) and side roller means (31, 32, 26), respectively, for slidable mounting on said guide frame.

3. Apparatus as defined in claim 1, wherein said coupling frame means has a generally U-shaped horizontal cross section, the forwardly extending legs thereof being connected with opposite sides of said bracket means.

4. Apparatus as defined in claim 3, wherein said spaced slot connecting means are arranged in said coupling frame means.

5. Apparatus as defined in claim 4, wherein said coupling frame means and said carriage means comprise a unitary coupling device, said drive means being connected with the forward portion thereof.

* * * * *